US007030296B2

(12) United States Patent
East

(10) Patent No.: US 7,030,296 B2
(45) Date of Patent: Apr. 18, 2006

(54) TOXIN GENE FROM THE BACTERIA PHOTORHABDUS LUMINESCENS

(75) Inventor: Peter David East, O'Connor (AU)

(73) Assignee: Commonwealth Scientific and Industrial Research Organisation, (AU)

(*) Notice: Subject to any disclaimer, the term of this patent is extended or adjusted under 35 U.S.C. 154(b) by 252 days.

(21) Appl. No.: 10/617,962

(22) Filed: Jul. 14, 2003

(65) Prior Publication Data

US 2004/0055036 A1 Mar. 18, 2004

Related U.S. Application Data

(63) Continuation of application No. 09/463,048, filed as application No. PCT/AU98/00562 on Jul. 17, 1998, now Pat. No. 6,630,619.

(30) Foreign Application Priority Data

Jul. 17, 1997 (AU) .................................... PO8088

(51) Int. Cl.
*C12N 15/82* (2006.01)
*C12N 15/31* (2006.01)
*C12N 1/00* (2006.01)
*C01H 5/00* (2006.01)

(52) U.S. Cl. ..................... 800/302; 435/243; 435/71.1; 536/23.7

(58) Field of Classification Search ................ 435/243, 435/71.1; 800/302; 536/23.7
See application file for complete search history.

(56) References Cited

U.S. PATENT DOCUMENTS 5,972,687 A * 10/1999 Smigielski et al. ...... 435/252.3

FOREIGN PATENT DOCUMENTS

WO WO 95/00647 1/1995
WO WO 97/17432 5/1997

OTHER PUBLICATIONS

B. Brunel et al., Fast and Accurate Identification of *Xenorhabdus* and *Photorhabdus Species* by Restriction Analysis of PCR-Amplified 16S rRNA Genes, Applied and Environmental Microbiology, vol. 63, Feb. 1997, pp. 574-580.

S. Henikoff, Unidirectional Digestion with Exonuclease III Creates Targeted Breakpoings for DNA Sequencing, Gene, vol. 28, 1984, pp. 351-359.

M.A. Innis et al., PCR Protocols: A guide to Methods and Applications, Academic Press, Inc. 1980, pp. 3-20.

(Continued)

*Primary Examiner*—Anne Kubelik
(74) *Attorney, Agent, or Firm*—McDermott Will & Emery LLP

(57) ABSTRACT

The invention relates to the identification and isolation of a polynucleotide molecule encoding a new class of protein insecticidal toxin produced by the bacteria *Photorhabdus luminescens*. The polynucleotide molecule may be incorporated into, for example, insect-specific viruses (including entomopox and nuclear polyhedrosis viruses), bacteria (including *Gracilicutes, Firmicutes, Tenericutes* and *Mendosicutes*), protozoa, yeast and plants for control of pest insects.

5 Claims, 10 Drawing Sheets

OTHER PUBLICATIONS

Figure 3:
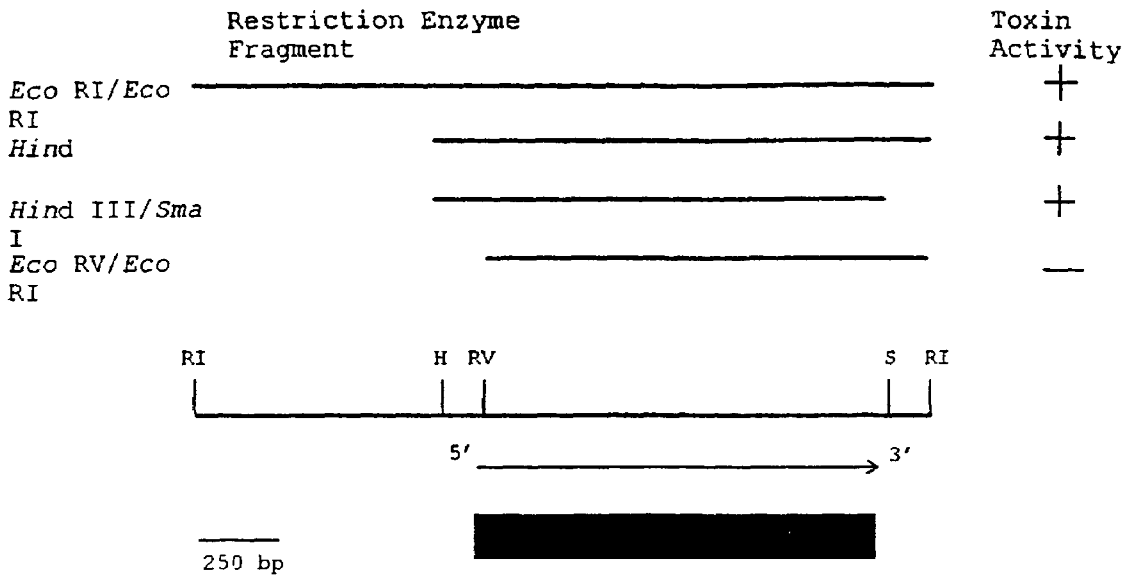

J. Marmur, A procedure for the Isolation of Deoxyribonucleic Acid from Micro-organisms, J. Mol. Biol., vol. 3, 1961, pp. 208-218.

K. F. Scott et al., Biological Nitrogen Fixation: Primary Structure of the *Klebsiella Pneumoniae nifH* and *nifO* Genes, Journal of Molecular and applied Genetics, vol. 1, pp. 71-81.

Lazar et al., Transforming growth factor a: mutation of aspartic acid 47 and leucine 48 resulted in different biological activities, Mar. 1988, pp. 1247-1252, vol. 8, No. 3.

Bowie et al., Deciphering the message in protein sequences: tolerance to amino acid substitutions Science, vol. 247.

Jouanin et al., Transgenic plants for Insect resistance Plant Science 131 1998 1-11.

Smigocki et al., cytokinin-mediated insect resistance in Nicotiana plants transformed with the pit gene 23: 325-335 1993.

Pang et al., Expression of a gene encoding a scorpion insectotoxin peptide in yeast, bacteria and plants Gene 116 1992 165-172.

Broun et al., Catalytic plasticity of fatty acid modification enzymes underlying chemical diversity of plant lipids, Science vol. 282, Nov. 13, 1998.

Hongsthong et al., "Optimum conditions for insecticidal toxin production by Photorhabdus Iuminescens" Abstracts of the General Meeting of the American Society for Microbiology, The Society, Washington, D.C., US, No. 95, May 1, 1995, pp. 408-AbstrQ-48, XP002076055 ISSN: 1060-2011.

Bowen D J et al., "Extracellular Insecticidal Factor Produced by Xenorhabdus Iuminescens" Abstracts of the Annual Meeting of the American Society For Microbiology, Washington, DC, US, vol. 90, 1989, p. 228 XP002119858 ISSN: 0094-8519.

Clarke David J. et al., "Virulence mechanism of Photorhabdus sp. strain K122 toward wax moth larvae." Journal of Invartebrate Pathology, vol. 66, No. 2, 1995, pp. 149-155, XP001064286 ISSN: 0022-2011.

Hu, K. et al., "Mortality of Plant-Parasitic Nematodes Caused by Bacterial (Xenorhabdus Spp. and Photorhabdus Luminescens) Culture Media" JournalOf Nematology, Socity of Nematologists, College Park, MD, US, vol. 27, No. 4, 1995, pp. 502-503. XP000905673 ISSN: 0022-300X.

David Joseph Bowen, "Characterization of a High Molecular Wieght Insecticidal Protein Complex Produced by the Entomopathogenic Bacterium Photorhabdus Luminescens (Nematodes, Biological Control)", Thesis University Wisconsin, XX, XX, May 1, 1995, XP002076022.

* cited by examiner

```
1     ATAATGGGAA AGTACAATGG TTATTAAACC CGTAACAACT CCGAGTGTAA
51    TACAATTAAC GCCTGATGAT AGAGTAACGC CTGATGATAA AGGTGAATAT
101   CAACCCGTTG AAAAGCAAAT AGCGGGAGAT ATAATACGTG TACTAGAATT
151   CAAGCAAACA AATGAAAGTC ATACAGGATT GTATGGAATT GCATATCGAG
                                       TOX F2
201   CTAAGAAAGT AATAATAGCA TATGCTTTAG CGGTAAGTGG TATTCATAAT
251   GTCTCTCAAC TTCCAGAAGA CTATTATAAA AATAAGGATA ACACAGGTAG
301   AATTTATCAA GAATACATGT CTAATCTTTT ATCTGCACTA TTGGGTGAGA
351   ATGGTGATCA AATTTCTAAA GATATGGCAA ATGATTTTAC CCAGAACGAA
401   CTGGAGTTTG GAGGTCAACG TCTTAAAAAT ACCTGGGATA TTCCTGATCT
451   TGAGAATAAA CTATTGGAAG ATTATTCAGA TGAAGATAAA TTATTAGCAC
                                                  TOX F1
501   TATATTTCTT TGCTTCACAA GAACTTCCAA TGGAGGCAAA TCAACAATCA
                                                  TOX R3
551   AATGCAGCAA ATTTTTTTAA AGTAATTGAT TTTTTACTTA TCTTATCTGC
601   TGTAACATCA CTGGGAAAAA GGATTTTTTC AAAAAATTTT TACAATGGTC
651   TAGAAACTAA ATCATTAGAG AATTATATTG AGAGAAAAAA ACTTTCTAAA
                                                TOX F3
701   CCTTTCTTTC GACCACCGCA GAAGTTACCT GATGGCAGAA CAGGCTACTT
751   GGCCGGTCCA ACAAAAGCGC CTAAATTGCC AACAACGTCT TCTACAGCAA
                                                  TOX R4
801   CAACGTCTAC AGCAGCTTCA TCTAATTGGA GAGTTAGTTT GCAAAAACTT
851   AGAGATAACC CATCCAGAAA TACATTTATG AAAATGGATG ATGCTGCAAA
901   ACGAAAATAT AGTTCATTTA TAAAAGAGGT ACAAAAGGGT AATGATCCAC
951   GTGCAGCAGC AGCAAGTATT GGTACAAAAA GCGGCAGTAA CTTCGAAAAA
1001  CTGCAAGGTA GAGATTTATA TAGTATAAGA CTAAGCCAAG AACACAGGGT
                                        A24AC1
1051  AACATTCTCC ATAAATAATA CTGACCAAAT AATGGAGATC CAAAGTGTTG
1101  GAACTCATTA CCAAAATATA TAACCTGATT TATAGTAGTG ATAAGACGTA
1151  AGATAAATAT GGAAGGTTGT AATTCTATTG CACTTCCTCA GAGGTGACCG
1201  CTCAG
```

FIGURE 1

```
  1 MVIKPVTTPS VIQLTPDDRV TPDDKGEYQP VEKQIAGDII RVLEFKQTNE
 51 SHTGLYGIAY RAKKVIIAYA LAVSGIHNVS QLPEDYYKNK DNTGRIYQEY
101 MSNLLSALLG ENGDQISKDM ANDFTQNELE FGGQRLKNTW DIPDLENKLL
151 EDYSDEDKLL ALYFFASQEL PMEANQQSNA ANFFKVIDFL LILSAVTSLG
201 KRIFSKNFYN GLETKSLENY IERKKLSKPF FRPPQKLPDG RTGYLAGPTK
251 APKLPTTSST ATTSTAASSN WRVSLQKLRD NPSRNTFMKM DDAAKRKYSS
301 FIKEVQKGND PRAAAASIGT KSGSNFEKLQ GRDLYSIRLS QEHRVTFSIN
351 NTDQIMEIQS VGTHYQNI
```

FIGURE 2

```
1     AAGCTTGCTA ATAATTCTTG CGTAAGTTAA TTTTACATTG AAATTAACGC
      Hind III
51    TTAAAAAGCC AGGGAAAACT CTATATTTAA AGTTGAAATT TATATTAGTA

101   GCGACAAATT GCGGAGTTTT CTGCCAGAAA TTTCATAGCT CAAATAAACA

151   TTAACATAAT GGAGAAATAT AATGGTTATA CAATTAACAC CTGATGATAG

201   AAGTGGATAT CCACCCGTTG AAAAGCAAAT AGCAGGAGAT ATAGTACGTA
            Eco RV
251   TACTAAACTT TAAGCAAACA GATGAGGGTC ATACAGCATC ATATGGAATT

301   GAATATCGAG CTAAGAAAAT AATATTAGCT TACGCTTTGG CTGTAAGTGG
                                                AC4R
351   TATTCATAAT GTATCTAAAC TTCCTGATGA CTATTATAAG AATAAAGAGA

401   CTGCTGAGAG AATTTATCAA GAATATATGT CTAATCTTTC ATCTGCACTA

451   TTAGGTGAAA ATGGTGATCA AATTTCTAAA GATATGGCAA ATGGTTTTTA
                 AC2F
501   TAAGAATGAA CTGGATTTTG AAGGTCAATA TCCTCAAAAC ATTTGGAATG

551   TTCCTGAGCT TGAAAATAAA CCATTGAGTG CTTATTCAGA TGACGATAAA
                                      AC7R
601   TTATTAGCAC TATATTTTTT CTCTGTACAG GAAATTCCAC TGGAGGAAAA

651   TCAACAATCA AATGCCGCAA GATTTTTTAA ATTAATTGAT TTCTTATTTA

701   CCTTATCTGC TGTAACTTCA CTGGGAAGGA GGATTTTTTC AAAAAACTTT

751   TACAATGGAT TAGAGGCTAA ATCATTAGAG AATTATATTG AGAGAAAAAA
                          AC6F
801   ACTTTCTAAA CCTTTCTTTC GACCACCGCA GAGATTACCT GATGGCAGAA

851   TAGGTTATTT GGCTGGACCA ACAGAAGCGC CTAAATGGAG AGTGAGTTTT
                           AC5R
901   AAAGAACTTA AAAATAACAA ATCTAGGAAT GGATTTTCTA ATATGGAAGG

951   GGCTGCAAAA CAAAAGTATA GTTCATTTAT AAAAGAGGTA CAAAAGGGTA

1001  ACGCTCCACA GACAGCAGCG AAAAGTATTG GTACAGCCAG TGGCAGTAAC

1051  CTGGAAAAAT TGCCGAATAA TTTATATAGT GTGAGGCTAA GCCAAAAAGA
                                                 AC3F
1101  CAGGGTAACC TTTACTCAAA ATGATACTGA CAATACAATG ACGGTTCATA
                                                  AC8R
1151  GTGTTGGAAC TCATTATAAA AATATATGAT GAGTAATCTC TGACTTCGAT

1201  TGACAGAGCA TTTTTAAGCT CTCATTTTCT CAACGGGAGT CTCATAAGGC

1251  GTTTTACTTT TCAAGCCACT ATGTGGTCTG TGATAATTGT AAAACGCCTT

1301  CTTTTAGCCA ATACACTTTA CTACCAAGAA AATATATACC CTATGGATTT
                  V16AC1
1351  CAAGATGGAT CGCGGCGGCA AGGGAGCGAA TCCCCGGG
                                          Sma I
```

FIGURE 4

```
  1  MVIQLTPDDR SGYPPVEKQI AGDIVRILNF KQTDEGHTAS YGIEYRAKKI
 51  ILAYALAVSG IHNVSKLPDD YYKNKETAER IYQEYMSNLS SALLGENGDQ
101  ISKDMANGFY KNELDFEGQY PQNIWNVPEL ENKPLSAYSD DDKLLALYFF
151  SVQEIPLEEN QQSNAARFFK LIDFLFTLSA VTSLGRRIFS KNFYNGLEAK
201  SLENYIERKK LSKPFFRPPQ RLPDGRIGYL AGPTEAPKWR VSFKELKNNK
251  SRNGFSNMEG AAKQKYSSFI KEVQKGNAPQ TAAKSIGTAS GSNLEKLPNN
301  LYSVRLSQKD RVTFTQNDTD NTMTVHSVGT HYKNI
```

FIGURE 5

```
17   ATGGTTATTAAACCCGTAACAACTCCGAGTGTAATACAATTAACGCCTGA  66
                                                      |
172  .................................................ATGGT 176

67   TGATAGAGTAACGCCTGATGATAAAGGTGAATATCAACCCGTTGAAAAGC  116
     |    | |||| ||||||||| | ||| ||||| |||||||||||||||
177  TATACAATTAACACCTGATGATAGAAGTGGATATCCACCCGTTGAAAAGC  226

117  AAATAGCGGGAGATATAATACGTGTACTAGAATTCAAGCAAACAAATGAA  166
     |||||||  ||||||||| |||||  ||||| ||  |||||||||  ||||
227  AAATAGCAGGAGATATAGTACGTATACTAAACTTTAAGCAAACAGATGAG  276

167  AGTCATACAGGATTGTATGGAATTGCATATCGAGCTAAGAAAGTAATAAT  216
     ||||||||  ||  ||||||||||  ||||||||||||||||||| ||||| |
277  GGTCATACAGCATCATATGGAATTGAATATCGAGCTAAGAAAATAATATT  326

217  AGCATATGCTTTAGCGGTAAGTGGTATTCATAATGTCTCTCAACTTCCAG  266
     ||| || ||||| || |||||||||||||||||||| ||| |||||||| |
327  AGCTTACGCTTTGGCTGTAAGTGGTATTCATAATGTATCTAAACTTCCTG  376

267  AAGACTATTATAAAAATAAGGATAACACAGGTAGAATTTATCAAGAATAC  316
     | |||||||||| ||||| || |   | |  ||||||||||||||||||
377  ATGACTATTATAAGAATAAAGAGACTGCTGAGAGAATTTATCAAGAATAT  426

317  ATGTCTAATCTTTTATCTGCACTATTGGGTGAGAATGGTGATCAAATTTC  366
     |||||||||||| |||||||||||||| |||| |||||||||||||||||
427  ATGTCTAATCTTTCATCTGCACTATTAGGTGAAAATGGTGATCAAATTTC  476

367  TAAAGATATGGCAAATGATTTTACCCAGAACGAACTGGAGTTTGGAGGTC  416
     ||||||||||||||||| |||| ||||  ||||| |||||| ||| |||||
477  TAAAGATATGGCAAATGGTTTTATAAGAATGAACTGGATTTTGAAGGTC  526

417  AACGTCTTAAAAATACCTGGGATATTCCTGATCTTGAGAATAAACTATTG  466
     ||  ||  | |||| |  ||| ||  ||||||| ||||| |||||| ||||
527  AATATCCTCAAAACATTTGGAATGTTCCTGAGCTTGAAAATAAACCATTG  576

467  GAAGATTATTCAGATGAAGATAAATTATTAGCACTATATTTCTTTGCTTC  516
     | |||||||||||||| |||||||||||||||||||||||   || ||
577  AGTGCTTATTCAGATGACGATAAATTATTAGCACTATATTTTTTCTCTGT  626

517  ACAAGAACTTCCAATGGAGGCAAATCAACAATCAAATGCAGCAAATTTTT  566
     ||| ||| ||||| ||||||  |||||||||||||||||||| |||| ||||
627  ACAGGAAATTCCACTGGAGGAAAATCAACAATCAAATGCCGCAAGATTTT  676
```

Figure 6A

```
567 TTAAAGTAATTGATTTTTTACTTATCTTATCTGCTGTAACATCACTGGGA 616
    ||||| |||||||||| ||| ||| ||||||||||||||| |||||||||
677 TTAAATTAATTGATTTCTTATTTACCTTATCTGCTGTAACTTCACTGGGA 726
              .         .         .         .         .
617 AAAAGGATTTTTTCAAAAAATTTTTACAATGGTCTAGAAACTAAATCATT 666
    |  ||||||||||||||||| |||||||||||  ||||  ||||||||||
727 AGGAGGATTTTTTCAAAAAACTTTTACAATGGATTAGAGGCTAAATCATT 776
              .         .         .         .         .
667 AGAGAATTATATTGAGAGAAAAAAACTTTCTAAACCTTTCTTTCGACCAC 716
    ||||||||||||||||||||||||||||||||||||||||||||||||||
777 AGAGAATTATATTGAGAGAAAAAAACTTTCTAAACCTTTCTTTCGACCAC 826
              .         .         .         .         .
717 CGCAGAAGTTACCTGATGGCAGAACAGGCTACTTGGCCGGTCCAACAAAA 766
    ||||||  |||||||||||||||| ||| || ||||| || |||||| ||
827 CGCAGAGATTACCTGATGGCAGAATAGGTTATTTGGCTGGACCAACAGAA 876
```

Figure 6A - Continued

```
767  GCGCCTAAATTGCCAACAACGTCTTCTACAGCAACAACGTCTACAGCAGC 816
877  GCGCCTAAA.........................................  885

817  TTCATCTAATTGGAGAGTTAGTTTGCAAAAACTTAGAGATAACCCATCCA 866
886  ..........TGGAGAGTGAGTTTTAAAGAACTTAAAAATAACAAATCTA 925

867  GAAATACATTTATGAAAATGGATGATGCTGCAAAACGAAAATATAGTTCA 916
926  GGAATGGATTTTCTAATATGGAAGGGGCTGCAAAACAAAAGTATAGTTCA 975

917  TTTATAAAAGAGGTACAAAAGGGTAATGATCCACGTGCAGCAGCAGCAAG 966
976  TTTATAAAAGAGGTACAAAAGGGTAACGCTCCACAGACAGCAGCGAAAAG 1025

967  TATTGGTACAAAAAGCGGCAGTAACTTCGAAAAACTGCAAGGTAGAGATT 1016
1026 TATTGGTACAGCCAGTGGCAGTAACCTGGAAAAATTGCCGAATA...ATT 1072

1017 TATATAGTATAAGACTAAGCCAAGAACACAGGGTAACATTCTCCATAAAT 1066
1073 TATATAGTGTGAGGCTAAGCCAAAAAGACAGGGTAACCTTTACTCAAAAT 1122

1067 AATACTGACCAAATAATGGAGATCCAAAGTGTTGGAACTCATTACCAAAA 1116
1123 GATACTGACAATACAATGACGGTTCATAGTGTTGGAACTCATTATAAAAA 1172

1117 TATATAA[...] 1123[0]
1173 TATATGA 1179
```

FIGURE 6B

```
             .         .         .         .         .
  1 MVIKPVTTPSVIQLTPDDRVTPDDKGEYQPVEKQIAGDIIRVLEFKQTNE 50
              |||||||||      ::|.||||||||||:|:|:||||:|
  1 .........MVIQLTPDDR......SGYPPVEKQIAGDIVRILNFKQTDE 35

             .         .         .         .         .
 51 SHTGLYGIAYRAKKVIIAYALAVSGIHNVSQLPEDYYKNKDNTGRIYQEY 100
    :||: |||.|||||:|:|||||||||||||.||:||||||:..:||||||
 36 GHTASYGIEYRAKKIILAYALAVSGIHNVSKLPDDYYKNKETAERIYQEY 85

             .         .         .         .         .
101 MSNLLSALLGENGDQISKDMANDFTQNELEFGGQRLKNTWDIPDLENKLL 150
    |||| |||||||||||||||||:| .|||:|:||  .|.|::|:|||| |
 86 MSNLSSALLGENGDQISKDMANGFYKNELDFEGQYPQNIWNVPELENKPL 135

             .         .         .         .         .
151 EDYSDEDKLLALYFFASQELPMEANQQSNAANFFKVIDFLLILSAVTSLG 200
    ..|||:|||||||||. ||:|:|.|||||||.|||:||||:.||||||||
136 SAYSDDDKLLALYFFSVQEIPLEENQQSNAARFFKLIDFLFTLSAVTSLG 185

             .         .         .         .         .
201 KRIFSKNFYNGLETKSLENYIERKKLSKPFFRPPQKLPDGRTGYLAGPTK 250
    :||||||||||||.|||||||||||||||||||||:|||||.|||||||.
186 RRIFSKNFYNGLEAKSLENYIERKKLSKPFFRPPQRLPDGRIGYLAGPTE 235

             .         .         .         .         .
251 APKLPTTSSTATTSTAASSNWRVSLQKLRDNPSRNTFMKMDDAAKRKYSS 300
    |||                 ||||:..|::|.|||.| .|::|||.||||
236 APK.................WRVSFKELKNNKSRNGFSNMEGAAKQKYSS 268

             .         .         .         .         .
301 FIKEVQKGNDPRAAAASIGTKSGSNFEKLQGRDLYSIRLSQEHRVTFSIN 350
    |||||||||.|..|| |||| ||||:|||.. :|||:||||..||||. |
269 FIKEVQKGNAPQTAAKSIGTASGSNLEKLPN.NLYSVRLSQKDRVTFTQN 317

             .
351 NTDQIMEIQSVGTHYQNI 368
    :||..|.::||||||.||
318 DTDNTMTVHSVGTHYKNI 335
```

FIGURE 7

SEQUENCE LISTING

```
<160> NUMBER OF SEQ ID NOS: 20

<210> SEQ ID NO 1
<211> LENGTH: 1107
<212> TYPE: DNA
<213> ORGANISM: Xenorhabdus nematophilus

<400> SEQUENCE: 1

atggttatta aacccgtaac aactccgagt gtaatacaat taacgcctga tgatagagta     60

acgcctgatg ataaaggtga atatcaaccc gttgaaaagc aaatagcggg agatataata    120

cgtgtactag aattcaagca aacaaatgaa agtcatacag gattgtatgg aattgcatat    180

cgagctaaga aagtaataat agcatatgct ttagcggtaa gtggtattca taatgtctct    240

caacttccag aagactatta taaaaataag gataacacag gtagaattta tcaagaatac    300

atgtctaatc ttttatctgc actattgggt gagaatggtg atcaaatttc taaagatatg    360

gcaaatgatt ttacccagaa cgaactggag tttggaggtc aacgtcttaa aaatacctgg    420

gatattcctg atcttgagaa taaactattg gaagattatt cagatgaaga taaattatta    480

gcactatatt tctttgcttc acaagaactt ccaatggagg caaatcaaca atcaaatgca    540

gcaaattttt ttaaagtaat tgattttttta cttatcttat ctgctgtaac atcactggga    600

aaaaggattt tttcaaaaaa tttttacaat ggtctagaaa ctaaatcatt agagaattat    660

attgagagaa aaaaactttc taaacctttc tttcgaccac cgcagaagtt acctgatggc    720

agaacaggct acttggccgg tccaacaaaa gcgcctaaat tgccaacaac gtcttctaca    780

gcaacaacgt ctacagcagc ttcatctaat tggagagtta gtttgcaaaa acttagagat    840

aacccatcca gaaatacatt tatgaaaatg gatgatgctg caaaacgaaa atatagttca    900

tttataaaag aggtacaaaa gggtaatgat ccacgtgcag cagcagcaag tattggtaca    960

aaaagcggca gtaacttcga aaaactgcaa ggtagagatt tatatagtat aagactaagc   1020

caagaacaca gggtaacatt ctccataaat aatactgacc aaataatgga gatccaaagt   1080

gttggaactc attaccaaaa tatataa                                        1107


<210> SEQ ID NO 2
<211> LENGTH: 1008
<212> TYPE: DNA
<213> ORGANISM: Photorhabdus luminescens

<400> SEQUENCE: 2

atggttatac aattaacacc tgatgataga agtggatatc cacccgttga aaagcaaata     60

gcaggagata tagtacgtat actaaacttt aagcaaacag atgagggtca tacagcatca    120
```

-continued

```
tatggaattg aatatcgagc taagaaaata atattagctt acgctttggc tgtaagtggt    180

attcataatg tatctaaact tcctgatgac tattataaga ataaagagac tgctgagaga    240

atttatcaag aatatatgtc taatctttca tctgcactat taggtgaaaa tggtgatcaa    300

atttctaaag atatggcaaa tggtttttat aagaatgaac tggattttga aggtcaatat    360

cctcaaaaca tttggaatgt tcctgagctt gaaaataaac cattgagtgc ttattcagat    420

gacgataaat tattagcact atatttttc tctgtacagg aaattccact ggaggaaaat    480

caacaatcaa atgccgcaag attttttaaa ttaattgatt tcttatttac cttatctgct    540

gtaacttcac tgggaaggag gatttttca aaaaactttt acaatggatt agaggctaaa    600

tcattagaga attatattga gagaaaaaaa ctttctaaac ctttctttcg accaccgcag    660

agattacctg atggcagaat aggttatttg gctggaccaa cagaagcgcc taaatggaga    720

gtgagtttta aagaacttaa aaataacaaa tctaggaatg gattttctaa tatggaaggg    780

gctgcaaaac aaaagtatag ttcatttata aaagaggtac aaaagggtaa cgctccacag    840

acagcagcga aaagtattgg tacagccagt ggcagtaacc tggaaaaatt gccgaataat    900

ttatatagtg tgaggctaag ccaaaaagac agggtaacct ttactcaaaa tgatactgac    960

aatacaatga cggttcatag tgttggaact cattataaaa atatatga                1008
```

```
<210> SEQ ID NO 3
<211> LENGTH: 368
<212> TYPE: PRT
<213> ORGANISM: Xenorhabdus nematophilus

<400> SEQUENCE: 3

Met Val Ile Lys Pro Val Thr Thr Pro Ser Val Ile Gln Leu Thr Pro
1               5                   10                  15

Asp Asp Arg Val Thr Pro Asp Asp Lys Gly Glu Tyr Gln Pro Val Glu
            20                  25                  30

Lys Gln Ile Ala Gly Asp Ile Ile Arg Val Leu Glu Phe Lys Gln Thr
        35                  40                  45

Asn Glu Ser His Thr Gly Leu Tyr Gly Ile Ala Tyr Arg Ala Lys Lys
    50                  55                  60

Val Ile Ile Ala Tyr Ala Leu Ala Val Ser Gly Ile His Asn Val Ser
65                  70                  75                  80

Gln Leu Pro Glu Asp Tyr Tyr Lys Asn Lys Asp Asn Thr Gly Arg Ile
                85                  90                  95

Tyr Gln Glu Tyr Met Ser Asn Leu Leu Ser Ala Leu Leu Gly Glu Asn
            100                 105                 110

Gly Asp Gln Ile Ser Lys Asp Met Ala Asn Asp Phe Thr Gln Asn Glu
        115                 120                 125

Leu Glu Phe Gly Gly Gln Arg Leu Lys Asn Thr Trp Asp Ile Pro Asp
    130                 135                 140

Leu Glu Asn Lys Leu Leu Glu Asp Tyr Ser Asp Glu Asp Lys Leu Leu
145                 150                 155                 160

Ala Leu Tyr Phe Phe Ala Ser Gln Glu Leu Pro Met Glu Ala Asn Gln
                165                 170                 175

Gln Ser Asn Ala Ala Asn Phe Phe Lys Val Ile Asp Phe Leu Leu Ile
            180                 185                 190

Leu Ser Ala Val Thr Ser Leu Gly Lys Arg Ile Phe Ser Lys Asn Phe
        195                 200                 205

Tyr Asn Gly Leu Glu Thr Lys Ser Leu Glu Asn Tyr Ile Glu Arg Lys
    210                 215                 220
```

-continued

```
Lys Leu Ser Lys Pro Phe Phe Arg Pro Pro Gln Lys Leu Pro Asp Gly
225                 230                 235                 240

Arg Thr Gly Tyr Leu Ala Gly Pro Thr Lys Ala Pro Lys Leu Pro Thr
                245                 250                 255

Thr Ser Ser Thr Ala Thr Thr Ser Thr Ala Ala Ser Ser Asn Trp Arg
            260                 265                 270

Val Ser Leu Gln Lys Leu Arg Asp Asn Pro Ser Arg Asn Thr Phe Met
        275                 280                 285

Lys Met Asp Asp Ala Ala Lys Arg Lys Tyr Ser Ser Phe Ile Lys Glu
    290                 295                 300

Val Gln Lys Gly Asn Asp Pro Arg Ala Ala Ala Ala Ser Ile Gly Thr
305                 310                 315                 320

Lys Ser Gly Ser Asn Phe Glu Lys Leu Gln Gly Arg Asp Leu Tyr Ser
                325                 330                 335

Ile Arg Leu Ser Gln Glu His Arg Val Thr Phe Ser Ile Asn Asn Thr
            340                 345                 350

Asp Gln Ile Met Glu Ile Gln Ser Val Gly Thr His Tyr Gln Asn Ile
        355                 360                 365


<210> SEQ ID NO 4
<211> LENGTH: 335
<212> TYPE: PRT
<213> ORGANISM: Photorhabdus luminescens

<400> SEQUENCE: 4

Met Val Ile Gln Leu Thr Pro Asp Asp Arg Ser Gly Tyr Pro Pro Val
1               5                   10                  15

Glu Lys Gln Ile Ala Gly Asp Ile Val Arg Ile Leu Asn Phe Lys Gln
            20                  25                  30

Thr Asp Glu Gly His Thr Ala Ser Tyr Gly Ile Glu Tyr Arg Ala Lys
        35                  40                  45

Lys Ile Ile Leu Ala Tyr Ala Leu Ala Val Ser Gly Ile His Asn Val
    50                  55                  60

Ser Lys Leu Pro Asp Asp Tyr Tyr Lys Asn Lys Glu Thr Ala Glu Arg
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asn Gly Phe Tyr Lys Asn
            100                 105                 110

Glu Leu Asp Phe Glu Gly Gln Tyr Pro Gln Asn Ile Trp Asn Val Pro
        115                 120                 125

Glu Leu Glu Asn Lys Pro Leu Ser Ala Tyr Ser Asp Asp Asp Lys Leu
    130                 135                 140

Leu Ala Leu Tyr Phe Phe Ser Val Gln Glu Ile Pro Leu Glu Glu Asn
145                 150                 155                 160

Gln Gln Ser Asn Ala Ala Arg Phe Phe Lys Leu Ile Asp Phe Leu Phe
                165                 170                 175

Thr Leu Ser Ala Val Thr Ser Leu Gly Arg Arg Ile Phe Ser Lys Asn
            180                 185                 190

Phe Tyr Asn Gly Leu Glu Ala Lys Ser Leu Glu Asn Tyr Ile Glu Arg
        195                 200                 205

Lys Lys Leu Ser Lys Pro Phe Phe Arg Pro Pro Gln Arg Leu Pro Asp
    210                 215                 220

Gly Arg Ile Gly Tyr Leu Ala Gly Pro Thr Glu Ala Pro Lys Trp Arg
```

-continued

```
225                 230                 235                 240

Val Ser Phe Lys Glu Leu Lys Asn Asn Lys Ser Arg Asn Gly Phe Ser
                245                 250                 255

Asn Met Glu Gly Ala Ala Lys Gln Lys Tyr Ser Ser Phe Ile Lys Glu
            260                 265                 270

Val Gln Lys Gly Asn Ala Pro Gln Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Thr Gln Asn Asp Thr Asp
305                 310                 315                 320

Asn Thr Met Thr Val His Ser Val Gly Thr His Tyr Lys Asn Ile
                325                 330                 335


<210> SEQ ID NO 5
<211> LENGTH: 1205
<212> TYPE: DNA
<213> ORGANISM: Xenorhabdus nematophilus

<400> SEQUENCE: 5

ataatgggaa agtacaatgg ttattaaacc cgtaacaact ccgagtgtaa tacaattaac      60

gcctgatgat agagtaacgc ctgatgataa aggtgaatat caacccgttg aaaagcaaat     120

agcgggagat ataatacgtg tactagaatt caagcaaaca aatgaaagtc atacaggatt     180

gtatggaatt gcatatcgag ctaagaaagt aataatagca tatgctttag cggtaagtgg     240

tattcataat gtctctcaac ttccagaaga ctattataaa aataaggata acacaggtag     300

aatttatcaa gaatacatgt ctaatctttt atctgcacta ttgggtgaga atggtgatca     360

aatttctaaa gatatggcaa atgattttac ccagaacgaa ctggagtttg gaggtcaacg     420

tcttaaaaat acctgggata ttcctgatct tgagaataaa ctattggaag attattcaga     480

tgaagataaa ttattagcac tatatttctt tgcttcacaa gaacttccaa tggaggcaaa     540

tcaacaatca aatgcagcaa atttttttaa agtaattgat tttttactta tcttatctgc     600

tgtaacatca ctgggaaaaa ggatttttttc aaaaaatttt tacaatggtc tagaaactaa     660

atcattagag aattatattg agagaaaaaa actttctaaa cctttctttc gaccaccgca     720

gaagttacct gatggcagaa caggctactt ggccggtcca acaaaagcgc ctaaattgcc     780

aacaacgtct tctacagcaa caacgtctac agcagcttca tctaattgga gagttagttt     840

gcaaaaactt agagataacc catccagaaa tacatttatg aaaatggatg atgctgcaaa     900

acgaaaatat agttcattta taaaagaggt acaaaagggt aatgatccac gtgcagcagc     960

agcaagtatt ggtacaaaaa gcggcagtaa cttcgaaaaa ctgcaaggta gagatttata    1020

tagtataaga ctaagccaag aacacagggt aacattctcc ataaataata ctgaccaaat    1080

aatggagatc caaagtgttg gaactcatta ccaaaatata taacctgatt tatagtagtg    1140

ataagacgta agataaatat ggaaggttgt aattctattg cacttcctca gaggtgaccg    1200

ctcag                                                                 1205


<210> SEQ ID NO 6
<211> LENGTH: 1388
<212> TYPE: PRT
<213> ORGANISM: Photorhabdus luminescens

<400> SEQUENCE: 6

Ala Ala Gly Cys Thr Thr Gly Cys Thr Ala Ala Thr Ala Ala Thr Thr
```

-continued

```
1               5                   10                  15

Cys Thr Thr Gly Cys Gly Thr Ala Ala Gly Thr Thr Ala Ala Thr Thr
            20                  25                  30

Thr Thr Ala Cys Ala Thr Thr Gly Ala Ala Ala Thr Thr Ala Ala Cys
        35                  40                  45

Gly Cys Thr Thr Ala Ala Ala Ala Ala Gly Cys Cys Ala Gly Gly Gly
    50                  55                  60

Ala Ala Ala Ala Cys Thr Cys Thr Ala Thr Ala Thr Thr Thr Ala Ala
65                  70                  75                  80

Ala Gly Thr Thr Gly Ala Ala Ala Thr Thr Thr Ala Thr Ala Thr Thr
                85                  90                  95

Ala Gly Thr Ala Gly Cys Gly Ala Cys Ala Ala Ala Thr Thr Gly Cys
            100                 105                 110

Gly Gly Ala Gly Thr Thr Thr Thr Cys Thr Gly Cys Cys Ala Gly Ala
        115                 120                 125

Ala Ala Thr Thr Thr Cys Ala Thr Ala Gly Cys Thr Cys Ala Ala Ala
    130                 135                 140

Thr Ala Ala Ala Cys Ala Thr Thr Ala Ala Cys Ala Thr Ala Ala Thr
145                 150                 155                 160

Gly Gly Ala Gly Ala Ala Ala Thr Ala Thr Ala Ala Thr Gly Gly Thr
                165                 170                 175

Thr Ala Thr Ala Cys Ala Ala Thr Thr Ala Ala Cys Ala Cys Cys Thr
            180                 185                 190

Gly Ala Thr Gly Ala Thr Ala Gly Ala Ala Gly Thr Gly Gly Ala Thr
        195                 200                 205

Ala Thr Cys Cys Ala Cys Cys Cys Gly Thr Thr Gly Ala Ala Ala Ala
    210                 215                 220

Gly Cys Ala Ala Ala Thr Ala Gly Cys Ala Gly Gly Ala Gly Ala Thr
225                 230                 235                 240

Ala Thr Ala Gly Thr Ala Cys Gly Thr Ala Thr Ala Cys Thr Ala Ala
                245                 250                 255

Ala Cys Thr Thr Thr Ala Ala Gly Cys Ala Ala Ala Cys Ala Gly Ala
            260                 265                 270

Thr Gly Ala Gly Gly Gly Thr Cys Ala Thr Ala Cys Ala Gly Cys Ala
        275                 280                 285

Thr Cys Ala Thr Ala Thr Gly Gly Ala Ala Thr Thr Gly Ala Ala Thr
    290                 295                 300

Ala Thr Cys Gly Ala Gly Cys Thr Ala Ala Gly Ala Ala Ala Ala Thr
305                 310                 315                 320

Ala Ala Thr Ala Thr Thr Ala Gly Cys Thr Thr Ala Cys Gly Cys Thr
                325                 330                 335

Thr Thr Gly Gly Cys Thr Gly Thr Ala Ala Gly Thr Gly Gly Thr Ala
            340                 345                 350

Thr Thr Cys Ala Thr Ala Ala Thr Gly Thr Ala Thr Cys Thr Ala Ala
        355                 360                 365

Ala Cys Thr Thr Cys Cys Thr Gly Ala Thr Gly Ala Cys Thr Ala Thr
    370                 375                 380

Thr Ala Thr Ala Ala Gly Ala Ala Thr Ala Ala Ala Gly Ala Gly Ala
385                 390                 395                 400

Cys Thr Gly Cys Thr Gly Ala Gly Ala Gly Ala Ala Thr Thr Thr Ala
                405                 410                 415

Thr Cys Ala Ala Gly Ala Ala Thr Ala Thr Ala Thr Gly Thr Cys Thr
            420                 425                 430
```

-continued

```
Ala Ala Thr Cys Thr Thr Thr Cys Ala Thr Cys Thr Gly Cys Ala Cys
        435                 440                 445

Thr Ala Thr Thr Ala Gly Gly Thr Gly Ala Ala Ala Ala Thr Gly Gly
    450                 455                 460

Thr Gly Ala Thr Cys Ala Ala Ala Thr Thr Thr Cys Thr Ala Ala Ala
465                 470                 475                 480

Gly Ala Thr Ala Thr Gly Gly Cys Ala Ala Ala Thr Gly Gly Thr Thr
                485                 490                 495

Thr Thr Thr Ala Thr Ala Ala Gly Ala Ala Thr Gly Ala Ala Cys Thr
            500                 505                 510

Gly Gly Ala Thr Thr Thr Thr Gly Ala Ala Gly Gly Thr Cys Ala Ala
        515                 520                 525

Thr Ala Thr Cys Cys Thr Cys Ala Ala Ala Ala Cys Ala Thr Thr Thr
    530                 535                 540

Gly Gly Ala Ala Thr Gly Thr Thr Cys Cys Thr Gly Ala Gly Cys Thr
545                 550                 555                 560

Thr Gly Ala Ala Ala Ala Thr Ala Ala Ala Cys Cys Ala Thr Thr Gly
                565                 570                 575

Ala Gly Thr Gly Cys Thr Thr Ala Thr Thr Cys Ala Gly Ala Thr Gly
            580                 585                 590

Ala Cys Gly Ala Thr Ala Ala Ala Thr Thr Ala Thr Thr Ala Gly Cys
        595                 600                 605

Ala Cys Thr Ala Thr Ala Thr Thr Thr Thr Thr Thr Cys Thr Cys Thr
    610                 615                 620

Gly Thr Ala Cys Ala Gly Gly Ala Ala Ala Thr Thr Cys Cys Ala Cys
625                 630                 635                 640

Thr Gly Gly Ala Gly Gly Ala Ala Ala Ala Thr Cys Ala Ala Cys Ala
                645                 650                 655

Ala Thr Cys Ala Ala Ala Thr Gly Cys Cys Gly Cys Ala Ala Gly Ala
            660                 665                 670

Thr Thr Thr Thr Thr Thr Ala Ala Ala Thr Thr Ala Ala Thr Thr Gly
        675                 680                 685

Ala Thr Thr Thr Cys Thr Thr Ala Thr Thr Thr Ala Cys Cys Thr Thr
    690                 695                 700

Ala Thr Cys Thr Gly Cys Thr Gly Thr Ala Ala Cys Thr Thr Cys Ala
705                 710                 715                 720

Cys Thr Gly Gly Gly Ala Ala Gly Gly Ala Gly Gly Ala Thr Thr Thr
                725                 730                 735

Thr Thr Thr Cys Ala Ala Ala Ala Ala Ala Cys Thr Thr Thr Thr Ala
            740                 745                 750

Cys Ala Ala Thr Gly Gly Ala Thr Thr Ala Gly Ala Gly Gly Cys Thr
        755                 760                 765

Ala Ala Ala Thr Cys Ala Thr Thr Ala Gly Ala Gly Ala Ala Thr Thr
    770                 775                 780

Ala Thr Ala Thr Thr Gly Ala Gly Ala Gly Ala Ala Ala Ala Ala Ala
785                 790                 795                 800

Ala Cys Thr Thr Thr Cys Thr Ala Ala Ala Cys Cys Thr Thr Thr Cys
                805                 810                 815

Thr Thr Thr Cys Gly Ala Cys Cys Ala Cys Cys Gly Cys Ala Gly Ala
            820                 825                 830

Gly Ala Thr Thr Ala Cys Cys Thr Gly Ala Thr Gly Gly Cys Ala Gly
        835                 840                 845
```

-continued

```
Ala Ala Thr Ala Gly Gly Thr Thr Ala Thr Thr Thr Gly Gly Cys Thr
    850                 855                 860

Gly Gly Ala Cys Cys Ala Ala Cys Ala Gly Ala Ala Gly Cys Gly Cys
865                 870                 875                 880

Cys Thr Ala Ala Ala Thr Gly Gly Ala Gly Ala Gly Thr Gly Ala Gly
                885                 890                 895

Thr Thr Thr Thr Ala Ala Ala Gly Ala Ala Cys Thr Thr Ala Ala Ala
            900                 905                 910

Ala Ala Thr Ala Ala Cys Ala Ala Ala Thr Cys Thr Ala Gly Gly Ala
        915                 920                 925

Ala Thr Gly Gly Ala Thr Thr Thr Thr Cys Thr Ala Ala Thr Ala Thr
    930                 935                 940

Gly Gly Ala Ala Gly Gly Gly Gly Cys Thr Gly Cys Ala Ala Ala Ala
945                 950                 955                 960

Cys Ala Ala Ala Ala Gly Thr Ala Thr Ala Gly Thr Thr Cys Ala Thr
                965                 970                 975

Thr Thr Ala Thr Ala Ala Ala Ala Gly Ala Gly Gly Thr Ala Cys Ala
            980                 985                 990

Ala Ala Ala Gly Gly Gly Thr Ala  Ala Cys Gly Cys Thr  Cys Cys Ala
        995                 1000                1005

Cys Ala  Gly Ala Cys Ala Gly  Cys Ala Gly Cys Gly  Ala Ala Ala
    1010                 1015                 1020

Ala Gly  Thr Ala Thr Thr Gly  Gly Thr Ala Cys Ala  Gly Cys Cys
    1025                 1030                 1035

Ala Gly  Thr Gly Gly Cys Ala  Gly Thr Ala Ala Cys  Cys Thr Gly
    1040                 1045                 1050

Gly Ala  Ala Ala Ala Ala Thr  Thr Gly Cys Cys Gly  Ala Ala Thr
    1055                 1060                 1065

Ala Ala  Thr Thr Thr Ala Thr  Ala Thr Ala Gly Thr  Gly Thr Gly
    1070                 1075                 1080

Ala Gly  Gly Cys Thr Ala Ala  Gly Cys Cys Ala Ala  Ala Ala Ala
    1085                 1090                 1095

Gly Ala  Cys Ala Gly Gly Gly  Thr Ala Ala Cys Cys  Thr Thr Thr
    1100                 1105                 1110

Ala Cys  Thr Cys Ala Ala Ala  Ala Thr Gly Ala Thr  Ala Cys Thr
    1115                 1120                 1125

Gly Ala  Cys Ala Ala Thr Ala  Cys Ala Ala Thr Gly  Ala Cys Gly
    1130                 1135                 1140

Gly Thr  Thr Cys Ala Thr Ala  Gly Thr Gly Thr Thr  Gly Gly Ala
    1145                 1150                 1155

Ala Cys  Thr Cys Ala Thr Thr  Ala Thr Ala Ala Ala  Ala Ala Thr
    1160                 1165                 1170

Ala Thr  Ala Thr Gly Ala Thr  Gly Ala Gly Thr Ala  Ala Thr Cys
    1175                 1180                 1185

Thr Cys  Thr Gly Ala Cys Thr  Thr Cys Gly Ala Thr  Thr Gly Ala
    1190                 1195                 1200

Cys Ala  Gly Ala Gly Cys Ala  Thr Thr Thr Thr Thr  Ala Ala Gly
    1205                 1210                 1215

Cys Thr  Cys Thr Cys Ala Thr  Thr Thr Thr Cys Thr  Cys Ala Ala
    1220                 1225                 1230

Cys Gly  Gly Gly Ala Gly Thr  Cys Thr Cys Ala Thr  Ala Ala Gly
    1235                 1240                 1245

Gly Cys  Gly Thr Thr Thr Thr  Ala Cys Thr Thr Thr  Thr Cys Ala
```

-continued

```
    1250                1255                1260

Ala Gly  Cys Cys Ala Cys Thr  Ala Thr Gly Thr Gly  Gly Thr Cys
    1265                1270                1275

Thr Gly  Thr Gly Ala Thr Ala  Ala Thr Thr Gly Thr  Ala Ala Ala
    1280                1285                1290

Ala Cys  Gly Cys Cys Thr Thr  Cys Thr Thr Thr Thr  Ala Gly Cys
    1295                1300                1305

Cys Ala  Ala Thr Ala Cys Ala  Cys Thr Thr Thr Ala  Cys Thr Ala
    1310                1315                1320

Cys Cys  Ala Ala Gly Ala Ala  Ala Ala Thr Ala Thr  Ala Thr Ala
    1325                1330                1335

Cys Cys  Cys Thr Ala Thr Gly  Gly Ala Thr Thr Thr  Cys Ala Ala
    1340                1345                1350

Gly Ala  Thr Gly Gly Ala Thr  Cys Gly Cys Gly Gly  Cys Gly Gly
    1355                1360                1365

Cys Ala  Ala Gly Gly Gly Ala  Gly Cys Gly Ala Ala  Thr Cys Cys
    1370                1375                1380

Cys Cys  Gly Gly Gly
    1385
```

<210> SEQ ID NO 7
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 7
ttagcggtaa gtggtattca t 21

<210> SEQ ID NO 8
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 8
aggcaaatca acaatcaaat g 21

<210> SEQ ID NO 9
<211> LENGTH: 20
<212> TYPE: DNA
<213> ORGANISM: Artificial Sequence
<220> FEATURE:
<223> OTHER INFORMATION: Derived from X. nematophilus

<400> SEQUENCE: 9
gacgtaaact aacaactaaa 20

<210> SEQ ID NO 10
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 10
tgatggcaga acaggctact t 21

<210> SEQ ID NO 11

-continued

<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 11
tctgcaacaa cgacatcttc t 21

<210> SEQ ID NO 12
<211> LENGTH: 20
<212> TYPE: DNA
<213> ORGANISM: Artificial Sequence
<220> FEATURE:
<223> OTHER INFORMATION: Derived from X. nematophilus

<400> SEQUENCE: 12
ggacacaaga accgaatcag 20

<210> SEQ ID NO 13
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 13
atggtgaatg tcggtttcgc 20

<210> SEQ ID NO 14
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 14
tgaactggat tttgaaggtc 20

<210> SEQ ID NO 15
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 15
gcagtagact tattcgtgag 20

<210> SEQ ID NO 16
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 16
ctttcgacca ccgcagagat 20

<210> SEQ ID NO 17
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 17

-continued

```
gtaaatccgc gaagacaacc                                                20


<210> SEQ ID NO 18
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 18

tgacggttca tagtgttgga                                                20


<210> SEQ ID NO 19
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 19

aggttgtgat acttggcagt                                                20


<210> SEQ ID NO 20
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 20

ccatcatttc acataaccga                                                20
```

TOXIN GENE FROM THE BACTERIA PHOTORHABDUS LUMINESCENS

This application is a continuation application of application Ser. No. 09/463,048 filed on Apr. 4, 2000, now U.S. Pat. No. 6,630,619, issued 7 Oct. 2003, which is the national phase application under U.S.C. §371 of PCT International Application No. PCT/AU98/00562 which has the International filing date of 17 Jul. 1998, which designated the United States of America and which claims priority to Application Ser. No. PO 8088 filed in Australia on 17 Jul. 1997.

FIELD OF THE INVENTION

The present invention concerns the identification and isolation of a new class of protein toxins with specificity for insects, which are produced by bacteria from the genera *Xenorhabdus* and *Photorhabdus*. In addition, the present invention relates to the incorporation of genes encoding this class of toxin into, for example, insect-specific viruses (including entomopox and nuclear polyhedrosis viruses), bacteria (including *Gracilicutes, Firmicutes, Tenericutes* and *Mendosicutes*), yeast and plants for control of insect pests.

BACKGROUND OF THE INVENTION

Insect pathogenic nematodes of the families *Steinernematidae* and *Heterorhabditidae* are known to be symbiotically associated with bacteria of the genera *Xenorhabdus* and *Photorhabdus* respectively. It has been observed that these bacteria have the ability to kill a wide range of different insects without the aid of their nematode partners. The present inventors have isolated polynucleotide molecules encoding a new class of protein insecticidal toxins from *Xenorhabdus nematophilus* strain A24 and *Photorhabdus luminescens* strain V16/1.

DISCLOSURE OF THE INVENTION

In a first aspect, the present invention provides an isolated polynucleotide molecule encoding an insecticidal toxin, said polynucleotide molecule comprising a nucleotide sequence which substantially corresponds to the nucleotide sequence shown as SEQ ID NO: 1 or SEQ ID NO: 2.

In a second aspect, the present invention provides an isolated polynucleotide molecule encoding an insecticidal toxin, said polynucleotide molecule comprising a nucleotide sequence having at least 85%, more preferably at least 95%, sequence identity to the nucleotide sequence shown as SEQ ID NO: 2.

In a third aspect, the present invention provides an insecticidal toxin, in a substantially pure form, which toxin comprises an amino acid sequence having at least 95% sequence identity to that shown as SEQ ID NO: 3.

In a fourth aspect, the present invention provides an insecticidal toxin, in a substantially pure form, which toxin comprises an amino acid sequence having at least 85%, more preferably at least 95%, sequence identity to that shown as SEQ ID NO: 4.

Most preferably, the insecticidal toxin of the third or fourth aspect comprises an amino acid sequence substantially corresponding to that shown as SEQ ID NO: 3 or SEQ ID NO: 4 respectively.

In a fifth aspect the present invention provides a recombinant microorganism, the recombinant microorganism being characterised in that it is transformed with and expresses the polynucleotide molecule of the first or second aspects of the present invention.

The microorganisms which may be usefully transformed with the polynucleotide molecule of the first or second aspects of the present invention include bacteria, such as *Escherichia, Gracilicutes, Firmicutes, Tenericutes* and *Mendosicutes;* protozoa and yeast. The microorganism can be transformed by routine methods using expression vectors comprising the toxin-encoding polynucleotide molecule operably linked to a suitable inducible or constitutive promoter sequence.

In a sixth aspect, the present invention provides a method of producing an insecticidal toxin, said method comprising:

(i) culturing a microorganism according to the fourth aspect under conditions suitable for the expression of the toxin-encoding polynucleotide molecule, and (ii) optionally recovering the expressed insecticidal toxin.

In a seventh aspect, the present invention provides a recombinant insect-specific virus, the recombinant insect-specific virus being characterised in that it includes within a non-essential region of its genome the polynucleotide molecule of the first or second aspects of the present invention operably linked to a suitable inducible or constitutive promoter sequence.

The recombinant insect-specific virus of the seventh aspect is preferably selected from entomopox and nuclear polyhedrosis viruses. The recombinant virus can be produced by routine methods such as homologous recombination.

In an eighth aspect, the present invention provides a method for killing pest insects, said method comprising applying to an area infested with said insects an effective amount of a recombinant microorganism according to the fourth aspect and/or a recombinant virus according to the seventh aspect, optionally in admixture with an acceptable agricultural carrier.

In a ninth aspect, the present invention provides a plant transformed with, and capable of expressing, the polynucleotide molecule of the first or second aspects of the present invention.

The plant according to the ninth aspect may be any plant of agricultural, arboricultural, horticultural or ornamental value that is susceptible to damage by feeding pest insects. However, preferably, the plant is selected from plants of agricultural value such as cereals (e.g.; wheat and barley), vegetable plants (e.g.; tomato and potato) and fruit trees (e.g., citrus trees and apples). Other preferred plants include tobacco and cotton.

The plant can be transformed by routine methods including *Agrobacterium* transformation and electroporation. Preferably, the toxin-encoding polynucleotide molecule is operably linked to a suitable inducible or constitutive promoter sequence. Particularly preferred promoter sequences include the cauliflower mosaic virus (CaMV 35S) promoter element and promoter elements from the sub-clover stunt virus (SCSV).

The term "substantially corresponds" as used herein in relation to the nucleotide sequence is intended to encompass minor variations in the nucleotide sequence which due to degeneracy do not result in a change in the encoded protein. Further this term is intended to encompass other minor variations in the sequence which may be required to enhance expression in a particular system but in which the variations do not result in a decrease in biological activity of the encoded protein.

The term "substantially corresponding" as used herein in relation to the amino acid sequence is intended to encompass minor variations in the amino acid sequence which do not result in a decrease in biological activity of the insecticidal toxin. These variations may include conservative amino acid substitutions. The substitutions envisaged are:

G, A, V, I, L, M; D, E; N, Q; S, T; K, R, H; F, Y, W, H; and P, Nα-alkalamino acids.

The term "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by way of reference to the following, non-limiting example and accompanying figures.

BRIEF DESCRIPTION OF THE ACCOMPANYING FIGURES

FIG. 1: Nucleotide sequence of the protein coding (sense) strand of the *X. nematophilus* DNA insert of clone tox4 (SEQ ID NO: 5). The translation initiation codon (ATG) at nucleotide position 17–19 and the translation termination codon (TAA) at nucleotide position 1121–1123 are indicated by shaded boxes. Locations of oligonucleotide sequences used for sequencing primer design are indicated by arrows and a primer name (TOX F2 (SEQ ID NO: 7), TOX F1 (SEQ ID NO: 8), TOX R3 (SEQ ID NO: 9), TOX F3 (SEQ ID NO: 10), TOX R4 (SEQ ID NO: 11), A24AC1 (SEQ ID NO: 12). Arrows directed left-to-right, positioned above the sequence indicate sense-strand primers, arrows directed right-to-left, positioned below the sequence indicate anti-sense primers.

FIG. 2: Deduced sequence of the 368 amino acid toxb4 protein from *X. nematophilus* strain A24, derived by conceptual translation of the long open reading frame commencing at nucleotide position 17 and ending at nucleotide position 1120 of the toxb4 gene sequence (FIG. 1) (SEQ ID NO: 3).

FIG. 3: Restriction map of *P. luminescens* V16/1 toxin gene clone showing location of putative toxin protein coding region (solid black box) and direction of transcription (arrow). RI=EcoRI, RV=EcoRV, H=Hind III, S=Sma I. Toxin production from clones containing selected restriction fragments is indicated above the restriction map (+, toxin activity; –, no toxin activity).

FIG. 4: Nucleotide sequence of the protein coding (sense) strand of the *P. luminescens* Hind III/Sma I DNA fragment (SEQ ID NO: 6). Translation initiation (ATG) and termination (TGA) codons are indicated by shaded boxes. Locations of oligonucleotide sequences used for sequencing primer design are indicated by arrows and a primer name as described in the brief description of FIG. 1 (AC4R (SEQ ID NO: 13). AC2F (SEQ ID NO: 14), AC7R (SEQ ID NO: 15), AC6F (SEQ ID NO: 16). AC5R (SEQ ID NO: 17). AC3F (SEQ ID NO: 18), AC8R (SEQ ID NO: 19), and V16AC1 (SEQ ID NO: 20)). Restriction enzyme sites used for subcloning and identification of sequences necessary for toxin activity are underlined and labeled on the figure.

FIG. 5: Deduced sequence of the 335 amino acid PlV16tox1 protein from *P. luminescens* strain V16/1, derived by conceptual translation of the long open reading frame commencing at nucleotide position 172 and ending at nucleotide position 1179 of the Hind III/Sma I restriction enzyme fragment (FIG. 4) (SEQ ID NO: 4).

FIGS. 6A and 6B: Alignment of the nucleotide sequences encompassing the protein open reading frames of the *X. nematophilus* strain A24toxb4 gene (SEQ ID NO: 1) and the *P. luminescens* strain V16/1 PlVi16tox1 gene (SEQ ID NO: 2) using the Gap program of the GCG computer software package. The *X. nematophilus* sequence is the upper line and the *P. luminescens* sequence is the lower line.

FIG. 7: Alignment of the deduced protein sequences of the extended open reading frames encoding the *X. nematophilus* A24 toxb4 protein (SEQ ID NO: 3) and the *P. luminescens* strain V16/1 P1V16tox1 protein (SEQ ID NO: 4) using the Gap program of the GCG computer software package. The *X. nematophilus* sequence is the upper line and the *P. luminescens* sequence is the lower line.

Figure 8:
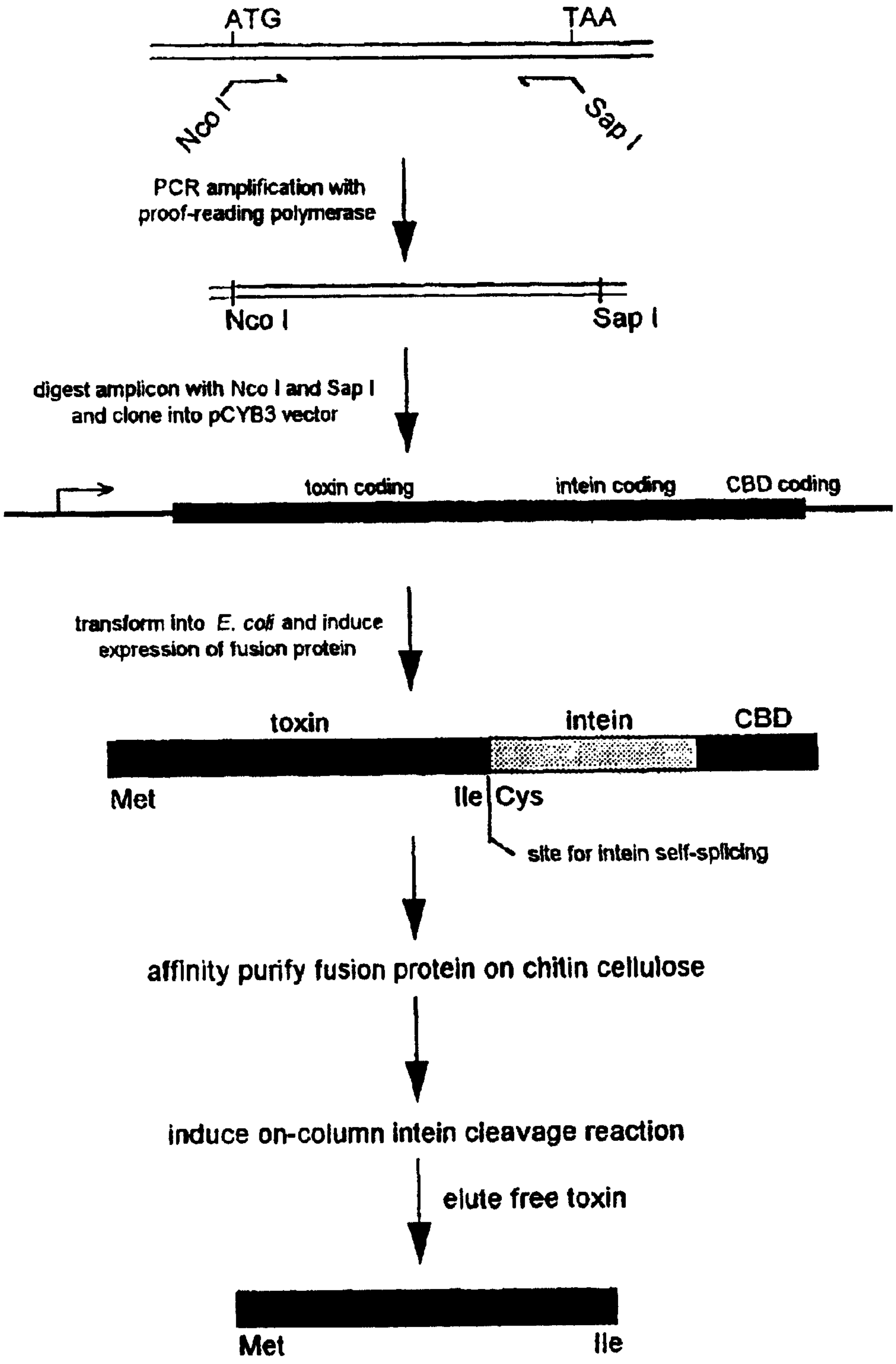

FIG. 8: Provides a scheme for expressing and isoltating *X. nematophilus* A24toxb4 protein and *P. luminescens* V16/7 PlV16tox1 protein using the IMPACT™ system. The toxin protein is represented schematically as a solid black bar with the first (Met) and last (Ile) amino acids indicated.

EXAMPLE 1

Isolation and Characterisation of Toxin genes from *Xenorhabdus nematophilus* A24 and *Photorhabdus luminescens*

Construction of Recombinant Bacterial DNA Libraries

High molecular weight genomic DNA was isolated from *Xenorhabdus nematophilus* strain A24 using the method of Marmur (1961) and from *Photorhabdus luminescens* strain V16/1 by the method of Scott et al. (1981). The genomic DNA was partially digested with the restriction enzyme Sau 3AI to generate fragments of DNA in the size range 30 to 50 kilobase pairs and dephosphorylated by incubation with the enzyme calf intestinal alkaline phosphatase. The cosmid cloning vector "Supercos" (Stratagene) was linearised by digestion with the restriction enzyme Bam HI and ligated to the partially digested bacterial DNA at a vector:genomic DNA ratio of 1:3 according to standard procedures (Maniatis et al., 1982). The ligated DNA was packaged in vitro using Gigapack II XL Packaging Extract according to manufacturer's instructions (Stratagene). The packaged DNA was transfected into the *Escherichia coli* strain NM554 ($F^-$, recA, araD139, Δ(ara, leu) 7696, Δlac Y74, galU–, galK–, hsr, $hsm^+$, strA, mcrA[–], mcrA[–]). Transfected bacteria were plated onto Luria Bertani (LB) agar medium containing 150 $\mu g\ ml^{-1}$ ampicillin, to select for bacteria containing recombinant cosmid clones.

Isolation of an Insect Toxin Gene from *Xenorhabdus nematophilus* Strain A24 by Functional Screening Cultures of bacteria harbouring individual cosmid clones were grown overnight at 28° C. in LB broth containing 150 $\mu g\ ml^{-1}$ ampicillin. The bacterial cultures were treated for 15 minutes with 2 $mg\ ml^{-1}$ lysozyme to create cell-free lysates. Five microlitre aliquots of these lysates were injected into the haemocoel of three *Galleria mellonella* fourth instar larvae. Two clones with insecticidal activity were identified. Control lysates prepared by lysozyme treatment of *E. coli* NM554 cells containing non-recombinant Supercos vector possessed no toxin activity in the *Galleria* bioassay.

Characterisation of Toxin Producing Clones

Cosmid DNA from toxin-expressing clones was isolated-using a standard alkaline lysis procedure (Maniatis et al., 1982). Isolated DNA was analysed by restriction enzyme digestion and agarose gel electrophoresis (Maniatis et al., 1982). Both cosmid clones appeared to contain the same region of approximately 34.6 kb of *X. nematophilus* genomic DNA. One clone, designated cos149 was chosen for further analysis.

A 7.4 kb Bam HI fragment from cos149 was ligated into the plasmid vector pGEM7Z(f)+(Promega Biotec) and transformed into the *E. coli* strain DH5a ($F^-$, F8odlac ZΔ M15, recA1, endA1, gyrA96, thi-1, hsdR17 [$rK\_mK_+$] supE44, relA1, deoR, Δ[lacZYA-argF] U169) using electroporation at 25 mF, 200 and 2.5 kV in a 0.2 cm cuvette in a Bio-Rad Gene Pulser. The resultant sub-clone was designated N8pGEM. Lysates prepared from *E. coli* cells containing the N8pGEM clone contained toxin as determined by the *Galleria* haemolymph injection bioassay.

A set of unidirectional deletion clones was prepared from N8pGEM according to the method of Henikoff (1984) using the Erase-a-base kit (Promega Biotec) and digestion with the enzymes Cla I and Sph I. Deleted DNA was recircularised by ligation with T4 DNA ligase and transformed into *E. coli* strain DH5α by electroporation as described above. Deletion sub-clones of varying sizes were identified and tested for toxin production using the *Galleria* bioassay. The smallest clone that retained toxin expression (designated tox 1) contained 1.5 kb of *X. nematophilus* DNA.

Plasmid DNA from the tox 1 clone was isolated, digested with the restriction enzymes Sac I and Hind III and directionally deleted with the Erase-a-base kit. A set of deleted clones was identified and tested for toxin production. The smallest clone retaining toxin activity (designated toxb4) contained 1.2 kb of *X. nematophilus* DNA. The toxb4 clone was sequenced on both strands with a combination of vector and gene-specific sequencing primers and ABI Prism™ di-deoxy dye-terminator sequencing mix (Applied Biosystems). Plasmid DNA was prepared by a standard alkaline lysis procedure (Maniatis et al., 1982), the double-stranded DNA was sequenced by a thermal cycle sequencing protocol, and sequencing reactions were analysed on an automated DNA sequencer (Applied Biosystems Model 377) according to manufacturer's instructions.

The toxb4 clone contained an insert 1205 bp in length (FIG. 1) which encoded a protein open reading frame of 368 amino acid residues (FIG. 2). Searches of the non-redundant Genbank nucleotide and protein databases were done for the toxb4 nucleotide and deduced protein sequences using the blastn, fasta and blastp, programs for DNA and protein sequences. No statistically significant similarity was detected between the *X. nematophilus* sequences and sequences present in the databases.

Isolation of a toxb4 Homologue from *Photorhabdus luminescens* Strain V16/1

The genomic DNA cosmid library prepared from *P. luminescens* strain V16/1 was screened by nucleic acid hybridisation using the toxb4 gene as a hybridisation probe. Two hundred clones were grown overnight at 37° C. on LB agar plates containing 150 μg $ml^{-1}$ ampicillin and the resultant bacterial clones were transferred to nylon membrane discs (Colony/Plaque Screen™, NEN DuPont) according to the manufacturer's protocol. Colonies were lysed in situ on the membranes by treatment with 0.5 N NaOH and neutralised with 1.0M Tris-Cl, pH 7.5, and the cosmid DNA was immobilised on the membranes by air drying. Filters were pre-hybridised in a solution consisting of 5×SSPE, 0.2% w/v skim-milk powder, 0.5% w/v SDS and 0.2% mg/ml denatured salmon sperm DNA at 68° C. for 3 hours. A hybridisation probe was prepared by radiolabelling approximately 100 ng of isolated toxb4 DNA with 50 μCi α-$^{32}$P-dATP by random-primed synthesis using the Gigaprime DNA labelling kit (GPK-1, Bresatec). Filters were incubated with the toxb4 probe in 5×SSPE, 0.2% w/v skim-milk powder, 0.5% w/v SDS and 0.2% mg/ml denatured salmon sperm DNA at 68° C. overnight. Filters were rinsed briefly in 2×SSC, and washed once for 15 min at room temperature in 2×SSC, 0.1% w/v SDS, once at 68° C. for 30 min in 0.5×SSC, 0.2% SDS. After a final rinse in 0.5×SSC filters were autoradiographed for 24 hours at −80° C. Three clones that hybridised with the toxb4 probe were identified. Cultures were grown for each clone and cell lysates were assayed for toxicity using the *Galleria* bioassay. Two clones, designated cos154 and cos160 showed toxin expression. Cosmid DNA was isolated from cos154 and cos160 and analysed by restriction enzyme digestion and Southern blot hybridisation. An 8.5 kb Not I restriction enzyme fragment that hybridised to the toxb4 probe was isolated from clone cos160 and sub-cloned into the Not I site of the plasmid vector pBC (KS)+(Stratagene). Further restriction enzyme mapping and bioassay resulted in identification of a 2.4 kb Eco RI fragment that contained all the sequences necessary for production of active toxin.

Characterisation of the *P. luminescens* Strain V16/1 Toxin Gene

Three additional sub-clones of the 2.4 kb Eco RI fragment were constructed and tested for toxin production (FIG. 3). A 1.65 kb Hind III/Eco RI fragment, a 1.39 kb Hind III/Sma I fragment and a 1.44 kb Eco RV/Eco RI fragment were each ligated into the plasmid vector pBluescript II (KS)+(Stratagene) and the ligated DNA was transformed into *E. coli* strain DH10B™ (Stratagene) ($F^-$ mcrA Δ(mrr-hsdRMS-mcrBC) F8odlacZΔM15 ΔlacX74 deoR recA1 araD139 Δ(ara, leu)7697 galU galKI$^-$ rpsL nupG). Cell lysates were prepared from cultures containing each of these sub-clones and bioassayed by haemocoel injection into *Galleria* larvae. Cultures containing the 1.65 kb Hind III/Eco RI fragment and the 1.39 kb Hind III/Sma I fragment expressed active toxin but cultures containing the 1.44 kb Eco RV/Eco RI fragment were inactive in the bioassay (FIG. 3). Thus, sequences located 5' to the Eco RV site of the *P. luminescens* V16/1 Hind III/Eco RI fragment are required for toxin expression from the plasmid pBluescript II (KS)+, whereas sequences 3' to the Sma I site are dispensable. The toxin gene is designated PlV16tox1 and the toxin protein encoded by this gene is designated PlV16tox1. A strategy was developed for sequencing the 1.39 kb Hind III/Sma I *P. luminescens* DNA fragment based on internal restriction enzyme sites and custom-synthesised oligonucleotide sequencing primers. The complete sequence of the 1.39 kb Hind III/Sma I fragment was determined on both strands (FIG. 4). Analysis of this DNA sequence identified a single long open reading frame 335 amino acid residues in length (FIG. 5).

Comparison of the Toxin Gene and Protein Sequences from *X. nematophilus* and *P. luminescens*

The DNA sequences corresponding to the deduced toxin protein open reading frames were compared for the two bacterial species using the 'Gap' program of the GCG software package. The two gene sequences are 83% identical in the coding region (FIG. 6) but show no significant similarity in the sequences immediately 5' and 3' of the extended open reading frame. The toxin protein sequences were likewise compared with the 'Gap' program and found to be 75% identical to each other and 86% similar if physico-chemically conservative amino acid differences were taken into consideration (FIG. 7). The existence of two extended insertion/deletion variants between the two proteins identifies amino acids that are not essential for toxic activity against *Galleria melonella.*

EXAMPLE 2

Distribution of the Toxin Gene from *X. nematophilus* A24

Genomic DNA was prepared from the type strain for each of four identified *Xenorhabdus* species, an additional unclassified *Xenorhabdus* species and six *Photorhabdus luminescens* strains selected to include at least one member of each of the major genetic groups identified by analysis of 16S ribosomal RNA genes (Brunel et al., 1997). The DNA was digested with restriction enzymes, fractionated by agarose gel electrophoresis and transferred to nylon membranes by the Southern blot method (Maniatis et al., 1982) The filters were hybridised with a probe prepared from the *X. nematophilus* A24 toxb4 gene. Hybridisation conditions were selected that would allow sequences with an average identity of approximately 65% to be detected. The results are shown in Table 1.

TABLE 1

| Bacterial species | Strain | Toxin gene† |
|---|---|---|
| *Xenorhabdus nematophilus* | A24 | + |
| *Xenorhabdus nematophilus* | AN6 | + |
| *Xenorhabdus poinarii* | G6 | − |
| *Xenorhabdus beddingii* | Q58 | − |
| *Xenorhabdus bovienii* | T28 | − |
| *Xenorhabdus* sp. | K77 | − |
| *Photorhabdus luminescens* | Hb | − |
| *Photorhabdus luminescens* | Hm | − |
| *Photorhabdus luminescens* | C1 | − |
| *Photorhabdus luminescens* | V16 | + |
| *Photorhabdus luminescens* | C8406 | + |
| *Photorhabdus luminescens* | K81 | + |

†+ indicates presence of hybridising DNA, − indicates absence of hybridisation of toxin gene probe.

Clearly, homologues of the toxin gene from *X. nematophilus* A24 is present in some species of the genus Xenorhabdus, and some, but not all isolates of *Photorhabdus luminescens.*

EXAMPLE 3

Activity of Toxin Genes Cloned into Plasmid Vectors and Transformed into *E. coli*

Active toxin protein was expressed when the A24 toxb4 clone or V16 tox1 genes were inserted into general plasmid vectors of the type pGEM (Promega Biotec) or pBluescript (Stratagene) and the recombinant plasmids transformed into *E. coli*. More specifically, the *X. nematophilus* toxin A24 toxb4gene was cloned into the plasmid pGEM7z and the *P. luminescens* V16 tox1 gene was cloned into pBluescript SK.

Preparation of Cell Extract

A culture of *E. coli* cells transformed with either a recombinant plasmid containing a toxin gene or a non-recombinant parent plasmid was grown overnight at 37° C. in nutrient broth. Lysozyme was added to the culture to a final concentration of 1 mg/ml and the mixture left at room temperature for 30 minutes to lyse the cells. The cleared lysate was used directly for bioassay.

Bioassay

Extracts were bioassayed using the intrahaemocoel injection assay. Ten microlitres of *E. coli* cell lysate were injected into the abdominal region of a *Galleria mellonella* larvae through an intersegmental membrane. Bioassays were done on lo larvae for each extract and injected larvae were held at 22° C. Mortality was recorded daily. Results are shown in Table 2.

TABLE 2

| | Percentage mortality | | | | |
|---|---|---|---|---|---|
| Toxin source | Day 1 | Day 2 | Day 3 | Day 4 | Day 5 |
| PlV16tox1 | 0 | 20 | 40 | 90 | 100 |
| pBluescript SK (control) | 0 | 10 | 10 | 10 | 20 |
| A24toxb4 | 10 | 10 | 10 | 100 | 100 |
| pGEM7z (control) | 0 | 0 | 10 | 20 | 20 |

Extracts prepared from *E. coli* cells transformed with recombinant plasmids containing the toxin gene from either *X. nematophilus* A24 or *P luminescens* strain V16/1 kill *G. mellonella* larvae and caused complete mortality of injected individuals five days after injection. Extracts prepared from cells containing only the plasmid vectors pBluescript SK or pGEM7z did not kill the larvae.

Effect of Temperature on Toxicity

Extracts were prepared from *E. coli* cells transformed either with cloned toxin genes or the empty plasmid vector controls and injected into *G. mellonella* larvae as described previously. The injected larvae were maintained at either 20° C. or 25° C. Results are shown in Table 3.

TABLE 3

| | | Percentage mortality | | | | | |
|---|---|---|---|---|---|---|---|
| Toxin source | Temp | Day 1 | Day 2 | Day 3 | Day 4 | Day 5 | Day 6 |
| PlV16tox1 | 20° C. | 0 | 10 | 25 | 60 | 90 | 100 |
| PlV16tox1 | 25° C. | 0 | 0 | 100 | 100 | 100 | 100 |
| pBluescript SK | 20° C. | 0 | 0 | 0 | 0 | 0 | 0 |
| pBluescript SK | 25° C. | 0 | 5 | 10 | 10 | 15 | 15 |
| A24toxb4 | 20° C. | 5 | 30 | 35 | 65 | 95 | 100 |
| A24toxb4 | 25° C. | 60 | 75 | 100 | 100 | 100 | 100 |
| pGEM7z | 20° C. | 0 | 5 | 5 | 5 | 5 | 5 |
| pGEM7z | 25° C. | 0 | 5 | 5 | 5 | 5 | 5 |

Extracts prepared from cells containing either the cloned toxin gene from *X. nematophilus* A24 or the *P. luminescens* V16 toxin gene killed all larvae within three days for larvae held at 25° C. or by six days for larvae maintained at 20° C. following injection. Control extracts prepared from cells containing only the cloning vectors pBluescript or pGEM7z did not cause significant larval mortality.

EXAMPLE 4

Toxin Activity Against Different Insect Species (1) *Helicoverpa armigera* (Lepidoptera:Noctuidae)

Bioassay

Extracts were bioassayed using the intrahaemocoel injection assay. Ten microlitres of *E. coli* cell lysate were injected into the abdominal region of fourth instar *Helicoverpa armigera* larvae through an intersegmental membrane. Bioassays were done on 24 larvae for each extract and injected animals were held at 27° C. Mortality was recorded daily. Results are shown in Table 4.

TABLE 4

| | Percentage mortality | | | |
|---|---|---|---|---|
| Toxin source | Day 1 | Day 2 | Day 3 | Day 4 |
| PlV16tox1 | 38 | 71 | 87 | 91 |
| pBluescript SK | 4 | 4 | 8 | 8 |
| A24toxb4 | 50 | 87 | 91 | 91 |
| pGEM7z | 0 | 0 | 0 | 0 |

Extracts prepared from *E. coli* cells transformed with recombinant plasmids containing the toxin gene from either *X. nematophilus* A24 or *P luminescens* strain V16/1 caused significant mortality to injected larvae within 24 hours after injection. All larvae died by 4 days following the injection, with the exception of a small number of "escapees" that resulted from leakage of injected material upon removal of the injection needle. Extracts prepared from cells containing only the plasmid vectors pBluescript SK or pGEM7z had no significant effect on *H. armigera* larvae.

(2) *Plodia interpunctella* (Lepidoptera:)

Bioassay

Extracts were bioassayed using the intrahaemocoel injection assay. Five microlitres of *E. coli* cell lysate were injected into the abdominal region of a final instar *Plodia interpunctella* larva through an intersegmental membrane. Bioassays were done on 20 wandering-stage larvae for each extract and injected animals were held at 26° C. Mortality was recorded daily. Results are shown in Table 5.

TABLE 5

| | Percentage mortality | | |
|---|---|---|---|
| Toxin source | Day 1 | Day 2 | Day 3 |
| PlV16tox1 | 20 | 90 | 100 |
| pBluescript SK | 0 | 0 | 0 |
| A24toxb4 | 75 | 95 | 100 |
| pGEM7z | 0 | 5 | 5 |

Extracts prepared from *E. coli* cells transformed with recombinant plasmids containing the toxin gene from either *X. nematophilus* A24 or *P luminescens* strain V16/1 caused significant mortality to injected larvae within 24 hours after injection. All larvae had died within 3 days. Extracts prepared from cells containing only the plasmid vectors pBluescript SK or pGEM7z had no significant effect on survival of *P. interpunctella* larvae.

(3) *Lucilia cuprina* (Diptera: Calliphoridae) Adults

Bioassay

Extracts were bioassayed using the intrahaemocoel injection assay. Five microlitres of *E. coli* cell lysate were injected into the abdomen of a 3 day old *Lucilia cuprina* female fly through an intersegmental membrane. Bioassays were done on 20 flies for each extract and injected animals were held at 25° C. Mortality was recorded daily. Results are shown in Table 6.

TABLE 6

| | Percentage mortality | | | |
|---|---|---|---|---|
| Toxin source | Day 1 | Day 2 | Day 3 | Day 4 |
| PlV16tox1 | 55 | 65 | 85 | 100 |
| pBluescript SK | 20 | 25 | 25 | 25 |
| A24toxb4 | 55 | 75 | 85 | 100 |
| pGEM7z | 30 | 60 | 65 | 65 |

Extracts prepared from *E. coli* cells transformed with recombinant plasmids containing the toxin gene from either *X. nematophilus* A24 or *P luminescens* strain V16/1 caused significant mortality to injected flies within 24 hours of injection. All flies died by 4 days after injection. Extracts prepared from cells containing only the plasmid vectors pBluescript SK or pGEM7z also caused significant mortality to the *L. cuprina* flies in the first 48 hours following injection. After this control mortality stabilised, there was no further deaths for the remainder of the test period. Additional experiments with saline injections showed that the early mortality in the control group resulted from physical damage to the flies as a result of the injection process.

(4) *Lucilia Cuprina* (Diptera:Calliphoridae) Larvae

Bioassay

Extracts were bioassayed using the intrahaemocoel injection assay. Five microlitres of *E. coli* cell lysate were injected into the abdominal cavity of wandering-stage final instar Lucilia cuprina larvae through an intersegmental membrane. Bioassays were done on 20 larvae for each extract and injected animals were held at 25° C. Mortality was recorded daily. Results are shown in Table 7.

TABLE 7

| | Percentage mortality | | | |
|---|---|---|---|---|
| Toxin source | Day 1 | Day 2 | Day 3 | Day 4 |
| PlV16tox1 | 35 | 45 | 75 | 80 |
| pBluescript SK | 25 | 30 | 30 | 30 |
| A24toxb4 | 10 | 35 | 90 | 95 |
| pGEM7z | 15 | 20 | 20 | 25 |

Extracts prepared from *E. coli* cells transformed with recombinant plasmids containing the toxin gene from either *X. nematophilus* A24 or *P luminescens* strain V16/1 caused significant mortality to injected larvae within 48 hours of injection. All larvae died by 4 days after injection, with the exception of a small number of "escapees" resulting from leakage at the time of needle withdrawal as previously described for *H. armigera*. As with the *L. cuprina* adults, extracts prepared from cells containing only the plasmid vectors pBluescript SK or pGEM7z caused significant mortality to the *L. cuprina* larvae in the first 48 hours following injection. After this, control mortality stabilised and there were no further deaths in this group of larvae for the remainder of the test period. As described above, experiments with saline injections showed that this early mortality in the control group resulted from physical damage to the larvae as a result of the injection process.

(5) *Aphis gossypii* (Hemiptera:Aphididae) Numphs

Bioassay

Extracts were prepared from *E. coli* cells containing either the *X. nematophilus* toxin gene or the empty plasmid vector pGEM7z. The extracts were incorporated into a defined liquid diet at a concentration of 10% by volume and aphids were provided ad libitum access to diet for a period of five days. Results are shown in Table 8.

TABLE 8

| Treatment | % Mortality at day 5 | Average Number of Moults |
|---|---|---|
| Control† | 10 | 1.9 |
| pGEM7z extract | 0 | 2 |
| A24toxb4 extract | 90 | 0.6 |

†an additional treatment consisting of diet supplemented with lysozyme at the same final concentration used to prepare the *E. coli* cell extracts was included as a control for any potential effects of the lysozyme.

The *X. nematophilus* A24 toxin effectively blocked growth as seen from the reduction in the number of nymphal moults, and by five days had killed most of the larvae. Thus, the *X. nematophilus* A24 toxin was orally insecticidal to *Aphis gossypii.*

EXAMPLE 5

Expression and Purification of the Full-length Toxin Protein from *X. nematophilus*

Further characterisation of the properties of the toxins encoded by the cloned genes from *X. nematophilus* A24 and *P. luminescens* V16/1 required expression of the full-length protein in a format that allowed for affinity purification of the toxin. This was achieved by expressing the full-length toxin as a fusion protein in which the fusion partner was used for affinity selection, and the toxin domain was cleaved off chemically after the purification stage. A suitable expression and purification system is the IMPACT™ system (New England Biolabs) in which the toxin open reading frame is cloned at the 5' end of a self-splicing intein coding sequence fused to a short DNA sequence encoding a chitin binding domain.

Recombinant plasmids containing both the *X. nematophilus* A24 toxin and the *P. luminescens* V16/1 toxin genes were prepared in the IMPACT™ vector pCYB3 (FIG. 8). Preparation of these constructs required the engineering of a unique restriction enzyme site at each end of the toxin open reading frame that enabled in-frame insertion of the toxin gene into the expression vector such that translation began at the Methionine initiation codon of the toxin protein and a cleavage site for protein splicing was placed immediately adjacent to the final residue of the toxin open reading frame. Expression of the fusion proteins in *E. coli*, preparation of bacterial cell extracts, affinity isolaton of the fusion proteins on chitin cellulose columns, on-column DTT-mediated cleavage of the fusion proteins and elution of the purified toxin proteins were all performed according to the manufacturer's instructions (IMPACT™ system manual, New England Biolabs)

For both toxin constructs a major protein product of the expected size (approximately 40 kDa) was detected by SDS polyacrylamide gel electrophoretic analysis of the column eluate. The preparations contained several other proteins but these comprised less than 10% of the total protein present in the samples as determined by Coomassie blue staining of the polyacrylamide gels. Approximately 750 μg of PlV16tox1 toxin and 1.5 mg of A24toxb4 toxin were isolated from one litre of *E. coli* broth cultures. Purified proteins were dialysed against phosphate-buffered saline and simultaneously concentrated by diafiltration to a final concentration of approximately 1 mg/ml on Millipore spin cartridges with a membrane nominal molecular weight cut-off of 10 kDa according to manufacturer's instructions (Millipore).

EXAMPLE 6

Biological Activity of Purified Toxin Proteins

Bioassay

The activity of the purified *X. nematophilus* and *P. luminescens* toxins were determined by intra-haemocoel injection bioassay on *Galleria mellonella* and *Helicoverpa armigera* larvae as described above. The toxin protein preparations were diluted in phosphate-buffered saline and 10 ml of protein solution was injected into each larva. Ten larvae were injected for each protein concentration and mortality was recorded at 12 hour intervals for six days after injection. Proteins were tested over a dose range from 1 nanogram ($10^{-9}$ g) to 1 microgram ($10^{-6}$ g) of protein per larva. An inert protein, *E. coli* maltose binding protein, was prepared in the IMPACT™ system, purified and concentrated according to the same methods used for the two toxin proteins. The purified maltose binding protein was used as a control for these experiments. The maltose binding protein did not cause larval mortality at any of the quantities tested. The results are shown in Tables 9 to 12.

TABLE 9

Effect of purified PlV16 tox1 toxin on *G. mellonella* larvae

| Protein Injected | Percentage Mortality Day 2 am | Day 2 pm | Day 3 am | Day 3 pm | Day 4 am | Day 4 pm | Day 5 am | Day 5 pm | Day 6 am |
|---|---|---|---|---|---|---|---|---|---|
| 1 ng | 0 | 0 | 0 | 0 | 0 | 0 | 0 | 0 | 0 |
| 10 ng | 0 | 0 | 0 | 0 | 0 | 0 | 0 | 0 | 10 |
| 20 ng | 0 | 10 | 10 | 20 | 20 | 20 | 20 | 30 | 30 |
| 100 ng | 0 | 0 | 30 | 40 | 60 | 70 | 80 | 80 | 100 |
| 200 ng | 0 | 0 | 44 | 56 | 56 | 78 | 100 | 100 | 100 |
| 1000 ng | 20 | 20 | 60 | 60 | 100 | 100 | 100 | 100 | 100 |

TABLE 10

Effect of purified A24 toxb4 toxin on *G. mellonella* larvae

| Protein Injected | Percentage Mortality Day 2 am | Day 2 pm | Day 3 am | Day 3 pm | Day 4 am | Day 4 pm | Day 5 am | Day 5 pm | Day 6 am |
|---|---|---|---|---|---|---|---|---|---|
| 1 ng | 0 | 0 | 0 | 0 | 0 | 0 | 0 | 0 | 0 |
| 10 ng | 0 | 0 | 0 | 0 | 0 | 0 | 0 | 0 | 0 |
| 20 ng | 0 | 0 | 10 | 20 | 20 | 40 | 60 | 70 | 80 |
| 100 ng | 10 | 10 | 20 | 30 | 30 | 50 | 90 | 100 | 100 |
| 200 ng | 0 | 0 | 0 | 0 | 50 | 70 | 70 | 90 | 100 |
| 1000 ng | 0 | 0 | 0 | 10 | 60 | 80 | 100 | 100 | 100 |

TABLE 11

| Effect of purified PlV16 tox1 toxin on *H. armigera* larvae | | | | | | | | |
|---|---|---|---|---|---|---|---|---|
| | Percentage Mortality | | | | | | | |
| Protein Injected | Day 1/am | Day 1/pm | Day 2/am | Day 2/pm | Day 3/am | Day 3/pm | Day 4/am | Day 4/pm |
| 1 ng | 0 | 0 | 0 | 0 | 0 | 0 | 0 | 0 |
| 10 ng | 0 | 0 | 0 | 0 | 0 | 0 | 0 | 0 |
| 20 ng | 0 | 10 | 10 | 10 | 10 | 10 | 10 | 10 |
| 100 ng | 30 | 30 | 50 | 50 | 60 | 70 | 70 | 70 |
| 200 ng | 0 | 0 | 80 | 80 | 80 | 80 | 80 | 80 |
| 1000 ng | 22 | 67 | 100 | 100 | 100 | 100 | 100 | 100 |

TABLE 12

| Effect of purified A24 toxb4 toxin on *H. armigera* larvae | | | | | | | | |
|---|---|---|---|---|---|---|---|---|
| | Percentage Mortality | | | | | | | |
| Protein Injected | Day 1/am | Day 1/pm | Day 2/am | Day 2/pm | Day 3/am | Day 3/pm | Day 4/am | Day 4/pm |
| 1 ng | 0 | 0 | 0 | 0 | 0 | 0 | 0 | 0 |
| 10 ng | 0 | 30 | 50 | 70 | 90 | 90 | 90 | 90 |
| 20 ng | 0 | 30 | 50 | 80 | 90 | 90 | 90 | 90 |
| 100 ng | 0 | 20 | 80 | 100 | 100 | 100 | 100 | 100 |
| 200 ng | 0 | 30 | 90 | 100 | 100 | 100 | 100 | 100 |
| 1000 ng | 20 | 60 | 100 | 100 | 100 | 100 | 100 | 100 |

Both the *X. nematophilus* A24 toxin and the *P. luminescens* V16/1 toxin killed a high percentage of larvae after a single injection of at least 20 ng of toxin protein per larva. Mortality was dependent on toxin type and concentration. *H. armigera* was sensitive to small quantities of *X. nematophilus* A24 toxin with high mortality at 10–20 ng of toxin per larva, but was less sensitive to *P. luminescens* V16/1 toxin where significant mortality was observed only for quantities greater than 20 ng of protein per larva. A similar pattern of sensitivity was observed for *G. mellonella* larvae. The time taken to kill the larvae of either species was not strongly dependent on the time since toxin injection, although larger amounts of toxin killed more quickly. However, at all quantities greater than, or equal to 20 ng per larva the insects were effectively dead, because the *H. armigera* larvae ceased feeding and *G. mellonella* larvae were unable to spin cocoon silk.

Thus, the proteins encoded by the A24 toxb4 genes of *X. nematophilus* and the PlV16 tox1 gene of *P. luminescens* encode toxin proteins that are effective insecticides, especially of lepidopterous larvae including *G. mellonella, H. armigera* and *P. interpunctella*, when delivered into insect haemocoel.

EXAMPLE 7

Effect of Purified Toxin on Insect Cells in Culture

The purified *X nematophilus* A24 toxin and *P. luminescens* V16/1 toxin and the maltose binding protein control were each tested for their effects on the growth and viability of insect cells in tissue culture. A sample of $10^4$ cells in the appropriate culture medium was mixed with the test proteins at several different concentrations and seeded into the wells of a 96-well tissue culture plate. Cells were allowed to grow for 24 hours at 25° C. and cells were counted in a haemocytometer and assessed visually for cell lysis. The results are shown in Table 13.

For all cell lines, at all protein concentrations tested the maltose binding protein control had no effect on cell growth or viability. Neither of the toxin proteins had any significant effect on cell growth or viability for the *Drosophila melanogaster* Schneider 2 cell line. The *X. nematophilus* A24 toxin caused significant cell growth inhibition and cytotoxicity to the lepidopteran High-Five cell line at concentrations above 0.1 μg/ml. The *P. luminescens* V16 toxin caused slight growth inhibition only at the highest concentration tested of 1 μg/ml. The *X. nematophilus* A24 toxin caused significant cell growth inhibition and cytotoxicity to the lepidopteran Sf9 cell line at concentrations above 0.001 μg/ml, and the *P. luminescens* V16 toxin was toxic to this cell line at concentrations of 0.1 μg/ml and higher. Thus, toxins of this family exhibit growth inhibitory and cytotoxic activity against insect cells in tissue culture, especially cell lines of lepidopteran origin. Similar tests with a mouse hybridoma cell line demonstrated slight growth inhibition only by the *X. nematophilus* A24 toxin, and only at the highest concentration tested of 1 μg/ml.

TABLE 13

| | Treatment | | |
|---|---|---|---|
| Cell Line | Toxin | Concentration μg/ml | Cells/well |
| Schneider 2 | PlV16tox1 | 0 | $4.1 \times 10^4$ |
| | " | 0.001 | ND[†] |
| | " | 0.1 | $4.1 \times 10^4$ |
| | " | 1 | $4.6 \times 10^4$ |
| Schneider 2 | A24toxb4 | 0 | $3.7 \times 10^4$ |
| | " | 0.001 | ND |
| | " | 0.1 | $3.6 \times 10^4$ |
| | " | 1 | $3.4 \times 10^4$ |
| High-Fives | PlV16tox1 | 0 | $3.8 \times 10^4$ |
| | " | 0.001 | ND |
| | " | 0.1 | $3.9 \times 10^4$ |
| | " | 1 | $2.9 \times 10^4$ |
| High-Fives | A24toxb4 | 0 | $8.2 \times 10^4$ |
| | " | 0.001 | $7.1 \times 10^4$ |
| | " | 0.1 | $2.5 \times 10^4$ |
| | " | 1 | $2.5 \times 10^4$ |
| Sf9 | PlV16tox1 | 0 | $3.6 \times 10^4$ |
| | " | 0.001 | $4.3 \times 10^4$ |
| | " | 0.1 | $7 \times 10^3$ |
| | " | 1 | $6 \times 10^3$ |
| Sf9 | A24toxb4 | 0 | $4.7 \times 10^4$ |
| | " | 0.001 | $1 \times 10^4$ |
| | " | 0.1 | $5 \times 10^3$ |
| | " | 1 | $6.5 \times 10^3$ |

[†]ND: cell numbers not determined

As will be appreciated by persons skilled in this field, the present invention provides a new class of toxins useful for genetically engineering a wide range of biological systems which will thus become more useful for control of pest insects detrimental to agricultural, aquatic and forest industries. This new class of toxin may be purified by one or more methods of protein purification well known in the art. Insecticidal fragments may be generated from the purified toxin using, for example, cleavage with trypsin or cyanogen bromide.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Brunel, B., Givaudin, A., Lanois, A., Akburst, R. J. and Boemare, N. (1997). Fast and accurate identification of Xenorhabdus and Photorhabdus species by restriction analysis of PCR-amplified 16S rRNA genes. *Applied and Envirnomental Microbiology* 63, 574–580.

Henikoff, S. (1984). Unidirectional digestion with exonuclease III creates targeted breakpoints for DNA sequencing, Gene 28, 351–359.

Innis, M. A., Gelford, D. H., Sminsky, J. J. and White, T. J. (1990). PCR Protocols: A Guide to Methods and Applications. Academic Press, San Diego.

Maniatis, T., Fritsch, E. F. and Sambrook, J. (1982). Molecular cloning: A laboratory manual. Cold spring Harbor Laboratory, Cold spring Harbor, N.Y.

Marmur J. (1961). A procedure for the isolation of deoxyribonucleic acid from micro organisms.

Scott, K. F., Rolfe, B. G. and Shine, J. (1981). Biological nitrogen fixation: primary structure of the *Klebsiella pneumoniae* nifH and nifD genes. J. Mol. Appl. Genet. 1, 71–81.

What is claimed is:

1. An isolated polynucleotide molecule encoding an insecticidal toxin, said polynucleotide molecule comprising the nucleotide sequence shown as SEQ ID NO:2.

2. A recombinant microorganism, the microorganism being characterised in that it is transformed with and expresses the polynucleotide molecule according to claim 1.

3. The recombinant microorganism according to claim 2, wherein the microorganism is selected from the group consisting of a bacterium, a protozoon and a yeast.

4. A method of producing an insecticidal toxin, said method comprising:

(i) culturing the microorganism according to claim 2 under conditions suitable for the expression of the polynucleotide molecule; and (ii) recovering the insecticidal toxin.

5. A plant transformed with, and capable of expressing the polynucleotide molecule according to claim 1.

* * * * *